United States Patent [19]
Thomason et al.

[11] Patent Number: 5,772,678
[45] Date of Patent: Jun. 30, 1998

[54] RETRACTABLE DISPOSABLE TIP REUSABLE TROCAR OBTURATOR

[75] Inventors: Rodger Thomason, Los Angeles; James E. Carter, Dana Point; Neil H. Naves, Mission Viejo; Mark J. Legome, Mission Viejo; Jose M. Velez, Mission Viejo, all of Calif.

[73] Assignee: Inlet Medical, Inc., Eden Praire, Minn.

[21] Appl. No.: 546,015

[22] Filed: Oct. 20, 1995

[51] Int. Cl.$^6$ ................................................ A61B 17/34
[52] U.S. Cl. ...................... 606/185; 604/164; 604/264
[58] Field of Search ............................... 606/184, 185; 604/161, 117, 164–167, 264, 272, 280; 128/750–755

[56] References Cited

U.S. PATENT DOCUMENTS

| | | |
|---|---|---|
| 1,640,311 | 8/1927 | Dawes . |
| 4,368,730 | 1/1983 | Sharrock . |
| 4,573,448 | 3/1986 | Kambin . |
| 4,872,451 | 10/1989 | Moore et al. . |
| 5,011,478 | 4/1991 | Cope . |
| 5,120,317 | 6/1992 | Luther . |
| 5,195,985 | 3/1993 | Hall . |
| 5,209,736 | 5/1993 | Stephens et al. . |
| 5,242,427 | 9/1993 | Bicwels ................................. 604/164 |
| 5,282,476 | 2/1994 | Terwilliger . |
| 5,300,078 | 4/1994 | Buelna . |
| 5,312,360 | 5/1994 | Behl . |
| 5,312,363 | 5/1994 | Ryan et al. . |
| 5,320,610 | 6/1994 | Yoon . |
| 5,336,176 | 8/1994 | Yoon . |
| 5,352,206 | 10/1994 | Cushieri et al. . |
| 5,364,372 | 11/1994 | Danks et al. . |
| 5,368,045 | 11/1994 | Clement et al. . |
| 5,385,151 | 1/1995 | Scarfone et al. . |
| 5,395,317 | 3/1995 | Kambin . |

*Primary Examiner*—William Lewis
*Attorney, Agent, or Firm*—Cislo & Thomas

[57] ABSTRACT

A manual dilating trocar uses an automatically retracting stylet. The stylet is threaded through a dilating obturator which is, in turn, inserted into a trocar sheath. A spring near the handle of the stylet serves to urge the stylet cutting tip into a retracted position so that it can be held within the dilating tip of the dilating obturator. When a surgeon seeks to pierce a body cavity so as to perform laparoscopic surgery or the like, the handle is engaged to overcome the bias of the spring so that the stylet's cutting tip is exposed. Upon piercing of the exterior body-cavity layer, the stylet may be withdrawn to ensure that no underlying organs or tissue are damaged by the sharp stylet tip. Once the dilation of the initial stylet wound has been completed and the trocar sheath has been introduced into the body cavity, the dilating obturator may also be removed from within the trocar sheath in order to provide a channel into the body cavity. In an alternative embodiment, the stylet may be spring biased to expose the cutting tip, and a lock pin may be used so that energy stored in the spring can be brought to bear upon the stylet and to deliver a sharp cutting thrust of the stylet tip against any tough or obstructive tissue.

15 Claims, 9 Drawing Sheets

RETRACTABLE DISPOSABLE TIP REUSABLE TROCAR OBTURATOR

BACKGROUND OF THE INVENTION

1. Field of the Invention

The present invention relates to instruments used for laparoscopic surgery and the like, and more particularly to a safer trocar that keeps its stylet cutting tip retracted inside the obturator/dilator until ready for use.

2. Description of the Related Art

With the advance of medical science, new surgical techniques have been developed that allow a surgeon access to the patient's internal organs without creating large surgical wounds in the patient. Some of these surgical techniques include those which are less invasive than those techniques which have been used previously. For such less invasive surgery, one practice is to provide one or more entry/exit points into the body cavity within which the surgery must be performed.

For laparoscopic surgery, it is common to puncture, or pierce, the abdominal wall (including the peritoneum) and adjoining skin-tissue layer in order to gain access to the abdominal cavity. Once such access has been established, the abdominal cavity is inflated, or insulated, by the pumping of gas into the abdominal cavity at a low pressure, somewhat above atmospheric pressure. Once the abdominal cavity has been insufflated, surgical instruments may be introduced through one or more channels with a televised display of the surgical area of interest made for the surgeon and support teams.

It is of great advantage to make the laparoscopic wounds as small as possible while allowing as much freedom of movement for the surgical instruments as possible. In order to minimize the surgical wound, stylets having extremely sharp cutting tips are used to pierce the abdominal wall and the adjoining epithelial layers. As the stylet's point is exceedingly sharp and as the peritoneum and other tissues provide a tough layer of tissue that may be difficult to penetrate, it is important to ensure that the force used on the stylet by the surgeon in order to pierce the abdominal wall does not continue once the peritoneum and adjoining tissues have been pierced. If the surgeon continues to press upon the stylet once the cutting tip pierces the abdominal wall, the stylet will continue to travel into the patient's abdominal cavity and will pierce, puncture, and injure all obstructing tissues and organs. This defeats the advantages of laparoscopic surgery by inflicting more injury upon the patient than is necessary in order to perform therapeutic measures.

Prior efforts have been made in order to achieve trocar obturators for laparoscopic surgery.

I. Yoon, U.S. Pat. No. 5,320,610

This reference is directed to an automatically retractable safety trocar having an automatically movable safety shield. Referring to the Figures, the trocar instrument 10 includes a portal sleeve 14 concentrically disposed around a trocar 12, with a safety shield 16 concentrically disposed between trocar 12 and portal sleeve 14. The safety shield 16 has a conically shaped, blunt distal end 62 with an opening formed therein for passage of the sharp tip 28 of trocar 12. The instrument has a large palm hub, or knob, 18. The trocar is displaced to an exposed position by displacement of the knob 92 until it locks, and the knob is rotated into the distal transverse slot portion 86, shown in FIG. 2. The physician may then utilize the device as a standard safety trocar for penetrating the wall of an anatomical cavity. Once the instrument has passed through the tissue, an operating spring 76 will move safety shield 16 distally, causing distal movement of operating flange 66 to engage trigger member 60 and flex arms 54 in an outward direction, whereby retraction of the spring 46 will automatically move the retraction plate and trocar to a retracted position.

R. Stephens, et al., U.S. Pat. No. 5,209,736

This reference is directed to a trocar assembly which is adaptable to accommodate small- and large-diameter implements. The trocar assembly 10 includes an outer trocar tube 12 and an inner trocar tube 14 which is extendable through the outer trocar tube 12. The inner trocar tube 14 defines an interior lumen 26 which has an open distal end portion 30, the distal end portion having a conical contour. As shown in the embodiment of FIGS. 10–11, the central lumen of the inner trocar tube accommodates passage of an obturator 116 therethrough, the obturator 116 having a distal end 168 which is sharpened to a point 170 whereby the trocar can pierce the skin and enter the body; then, subsequently, the obturator 116 is removed.

R. Behl, U.S. Pat. No. 5,312,360

This reference is directed to a dilator assembly for enlarging percutaneous penetrations into body cavities. As shown, the dilator 30 has an axially directed lumen 34 which exits at the tapered distal end 32. A stylet 11 having a sharpened distal end 12 is received within an axial lumen 15 of a tubular guide member 16, the tubular guide member 16 being insertable into the lumen 34 of dilator 30. Although not spring driven, the stylet 11 permits the assembly to penetrate a body cavity wall and then be withdrawn after the dilator has been sufficiently advanced through the tissue.

I. Yoon, U.S. Pat. No. 5.336.176

This reference is directed to an automatically retractable safety trocar. In the embodiment of FIG. 1, a solid or cannulated needle 32 is axially displaceable within the cannula 34 for penetrating an anatomical cavity. A spring 54 formed by a resilient, tubular sleeve biases the needle distally to an extended position, such that the sharp tip 40 protrudes beyond the distal end of cannula 34. The needle 32 is retracted by means of the elastic spring member 60, responsive to operation of the retracting mechanism which includes the trigger mechanism 80.

T. Clement, et al., U.S. Pat. No. 5.368.045 and R. Terwilliger, U.S. Pat. No. 5,282,476

These references are directed to biopsy-needle instruments having spring-driven stylets. Both references disclose stylets and cannulas which are driven forward under spring force. In the '045 reference, the stylet is driven into the desired tissue site, such being immediately followed by the cannula. In the '476 reference, the cannula is driven forward relative to the stylus until the cannula has advanced a predetermined distance, at which point the stylet tracks the forward motion of the advancing cannula, both moving together for the remaining forward displacement of the cannula.

J. Hall, U.S. Pat. No. 5.195.985 and T. Buelna, U.S. Pat. No. 5.300.078

These references are directed to surgical devices and, in particular, handle structures therefor.

F. Scarfone, et al., U.S. Pat. No. 5,385,151

This reference is directed to a coaxial bone-marrow biopsy assembly. Although the assembly 10 includes a trocar 20, this reference discloses a handle 18 having a smooth upper surface 44 which is adapted to rest comfortably in a physician's palm, so that sufficient pressure can be applied to the trocar.

While the all these prior patents provide some measure of protection against inadvertent piercing of tissues adjacent the abdominal wall or other body cavity layer, generally, they do not provide removable and disposable stylets that can be used safely and easily and which do not require the surgeon to exert too much force in order to pierce any tough or obstructive tissues. In order to advance the art and to provide a more useful surgical tool, the present invention addresses these shortcomings and allows the surgeon to penetrate difficult or obstructive tissues without applying dangerous force upon the stylet cutting tip.

SUMMARY OF THE INVENTION

The present invention provides a trocar obturator that uses a disposable tip. The disposable tip allows the trocar obturator to always have the sharpest possible point, making the piercing, or puncturing, of a body cavity much easier and more consistent.

A stylet having an exceedingly sharp tip is closely surrounded by a dilating obturator having a sloped end. The stylet has a handle with a spring. When the stylet is inserted into the dilating obturator, it slides the length of the trocar until the cutting tip of the stylet approaches sloped end of the dilating obturator. The spring engages the adjacent end of the dilating obturator and urges the cutting tip to remain inside the end of the sloped tip of the dilating obturator. This keeps the exceedingly sharp cutting tip of the stylet recessed within the dilating obturator and yet allows the cutting tip to be exposed, when so desired by the surgeon, by pressing the handle toward the dilating obturator. The stylet and its cutting tip may be manipulated by the handle attached thereto.

The dilating obturator fits within a trocar sheath that provides a handle to the surgeon for the entire device. The trocar sheath has a gas, or access, port that may have a Luer fitting in order to maintain insufflation of the patient.

In use, the trocar obturator of the present invention is constructed by sliding the stylet into the dilating obturator and the dilating obturator into the trocar sheath. The surgeon then engages the stylet handle to expose the tip of the exceedingly sharp cutting tip past the angled end of the dilating obturator. The stylet cutting tip is then brought to bear upon the exterior of a body cavity to be pierced by the trocar obturator. The exposed cutting tip of the stylet is pressed against the body cavity exterior to pierce and puncture it. When the perforation is made, the extreme tip end of the dilating obturator follows the sharp cutting tip of the stylet into the body cavity through the surgical wound. Once the exterior has been completely punctured by the stylet tip and the tip end of the dilating obturator is within the body cavity, the stylet may be removed from inside the dilating obturator and the puncture wound dilated by the angled end of the dilating obturator.

The dilation of the surgical wound by the tip of the dilating obturator serves to mediate the transition between the cutting tip of the stylet and open end of the trocar sheath. Once the trocar sheath end is introduced past the wall of the body cavity and into the body cavity itself, the dilating obturator may be removed from within the trocar sheath and a stable channel, or path, into the body cavity is established and maintained by the trocar sheath. By affixing various lines to the access port with its Luer fitting, various materials, or substances, may be introduced into the body cavity through the trocar sheath. Alternatively, instruments may be introduced through the trocar sheath into the body cavity so laparoscopic or other surgery may be performed while invading the body to the least extent possible.

To avoid having to apply pressure to the entire device to safely pierce any tough or obstructive tissue surrounding the body cavity, an alternative embodiment allows the stylet to be slightly withdrawn from the dilating obturator, biasing a spring. Upon release of the stylet handle, the spring bias is allowed to quickly restore the stylet to its equilibrium position, throwing the exceedingly sharp cutting tip of the stylet past the opened end of the dilating obturator and against any obstructive tissue. The exceedingly sharp cutting tip of the stylet may then pierce or cut such tissue and allow the tip end of the dilating obturator to be introduced past the tough or obstructive tissue. In this way, the surgeon does not rely upon the strength of his arm to achieve the surgical puncture into the body cavity, which could result in a catastrophic injury should the obstructive tissue suddenly give way and the force behind the sharp stylet cutting tip not be stopped immediately. Instead, a short, sharp thrust of the exceedingly sharp cutting tip of the stylet is allowed to occur in order to form an initial puncture or cut in the obstructive tissue. This process may be repeated safely until a puncture wound of a sufficient depth allows the very tip of the dilating obturator to be introduced past the tough or obstructive tissue. Subsequently, the stylet may be removed and the dull and safe end of the dilating obturator may be forced into the puncture wound in order to dilate it and introduce the trocar sheath into the body cavity.

In alternative embodiments, a dilating obturator may be used that has a lock pin in order to store the thrusting force of the spring until ready to be released by the surgeon. Additionally, a trocar obturator may be constructed that uses a first spring to urge the exceedingly sharp stylet cutting tip against the exterior of the body cavity; and when tougher obstructive tissue is encountered, the retraction of the stylet under the influence of such tissue releases the force of the second spring; and such force is then transmitted to the stylet to press the exceedingly sharp cutting tip against the obstructive tissue to thereby puncture or pierce it.

In all embodiments, the extent to which the exceedingly sharp cutting tip of the stylet is exposed beyond the tip end of the dilating obturator is controlled so that only a very small portion of the stylet, namely, only its cutting tip, is exposed. Once the dilating obturator has been introduced past the tissue composing the exterior of the body cavity, the stylet is withdrawn so that no piercing, puncturing, or injury of underlying internal organs can take place. As the tip end of the dilating obturator is dull, pressure by it upon an adjacent organ or anatomical structure generally does not inflict any injury, which would occur with the sharp cutting tip of the stylet.

OBJECTS OF THE INVENTION

It is an object of the present invention to provide a sharp stylet that can be advanced and retracted independently of a dilator/obturator cannula so that a channel through tissue can be safely cut and the cutting tip removed before the dilator/obturator and cannula are advanced toward vulnerable internal organs.

It is an object of the present invention to provide a trocar obturator that may be safely used and which minimizes the risk of injury should the trocar obturator slip with an exposed cutting tip injuriously engaging underlying organs or anatomical structures.

It is another object of the present invention to provide a trocar obturator with a retracting tip.

It is yet another object of the present invention to provide a trocar obturator that uses a disposable stylet.

It is yet another object of the present invention to provide a trocar obturator that can safely pierce obstructive tissue with an exceedingly sharp cutting tip.

It is another object of the present invention to provide a trocar obturator that can safely pierce obstructive tissue by short, sharp thrusts of an exceedingly sharp stylet cutting tip.

It is yet another object of the present invention to provide a trocar obturator that limits the extent to which the cutting tip of the stylet may protrude from the end of the trocar obturator.

These and other objects and advantages of the present invention will be apparent from a review of the following specification and accompanying drawings.

DESCRIPTION OF THE PREFERRED EMBODIMENTS

Figure 1:
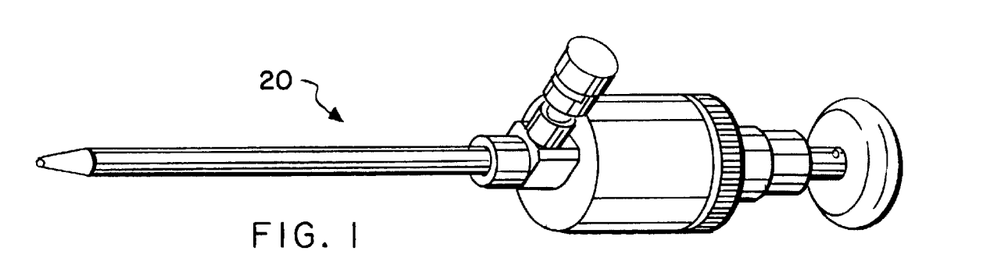
FIG. 1 shows a perspective view of the assembled trocar obturator of the present invention.

As can be seen in FIG. 1, the retractable disposable tip reusable trocar obturator 20 has several features and constructs that provide the advantages of a safe and useful trocar obturator.

Figure 2A:
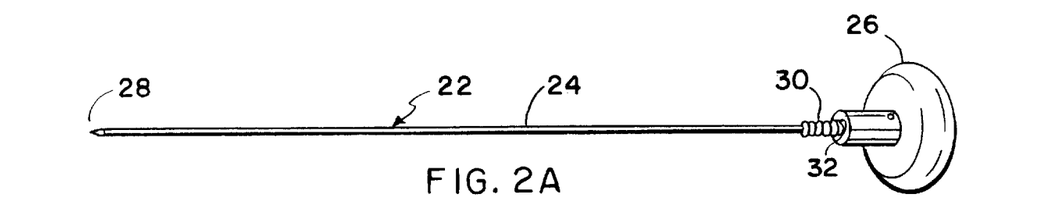
FIGS. 2A, 2B, and 2C show respectively: the stylet, the dilating obturator, and the trocar sheath.
Figure 2B:
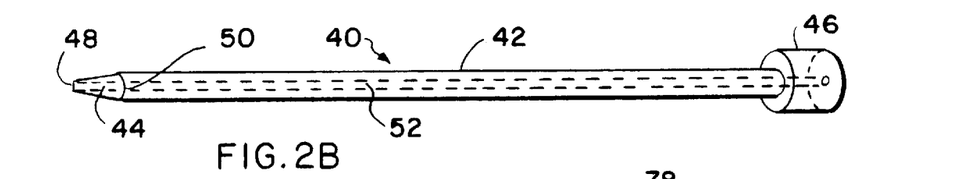
Figure 2C:
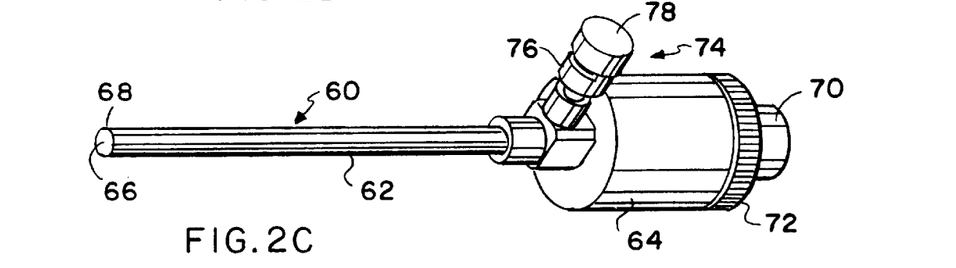

FIGS. 2A, 2B, and 2C show the three main portions of the present invention.

In FIG. 2A, the narrow stylet of the present invention is shown with its retraction spring and handle. The narrow stylet 22 is as thin as possible while maintaining structural integrity and without being overly flimsy. The stylet 22 has a shaft 24 that extends from the handle 26 to the sharp cutting tip 28 of the stylet 22. The cutting tip 28 of the stylet 22 is exceedingly sharp so that it encounters very little resistance as it passes through adjacent tissue. With such a narrow stylet, a very small incisor is provided to the surgeon so that he or she may have a very fine touch with respect to the use of the trocar obturator 20. By allowing the surgeon greater control over the insertion of the trocar obturator, safety is added to the surgery. Additionally, a smaller initial wound is created, thereby reducing the healing time once the surgical operation is completed.

Captured upon the stylet shaft 24 is a retraction spring 30 which may be connected to the handle 26 at a portion 32 where the stylet shaft 24 meets the handle 26. The function of the retraction spring is given in more detail below with respect to retracting the cutting tip 28 from the end of the dilating obturator.

FIG. 2B shows the dilating obturator 40. The dilating obturator has a shaft 42 that terminates at its distal end in a dilating tip 44. At the proximate end of the dilating obturator 40 is a stop block 46 that is concentric and coaxial with the shaft 42. The dilating tip is gently angled from the narrow aperture 48 to the distal end of shaft 42 at its full diameter 50.

Running completely through the center of the shaft 42 is a bore 52. The bore 52 is slightly wider than the diameter of the stylet shaft 24. (The close fit between bore 52 and stylet shaft 24 may provide support for the stylet shaft 24 as it engages tissue at the cutting tip 28, but support is not generally required.) While there is a close fit between the walls of bore 52 and the stylet shaft 24, stylet shaft 24 may turn and slide within the bore 52.

The stop block 46 has a cavity into which the retraction spring 30 and a portion of the handle 26 may fit. The retraction spring 30 does not enter into the bore 52 but is obstructed by the shaft 42 surrounding the bore 52.

When the retraction spring 30 is entirely compressed against the juncture 32 where the stylet shaft 24 meets the handle 26, the cutting tip 28 extends just beyond the aperture 48 to expose the cutting tip 28. When pressed into the dilating obturator 40, the handle portion present at the juncture 32 between the stylet shaft 24 and the handle 26 abuts against the shaft 42, preventing further travel of the stylet shaft 24 into the dilating obturator shaft 42. In this way, the extent of travel of the shaft 24 is limited, and the cutting tip 28 can only extend slightly past the aperture 48 present at the dilating tip 44 of the dilating obturator 40.

FIG. 2C shows the trocar sheath 60 with its cannula 62 and handle 64. The lumen 66 of the cannula 62 ends in a distal opening 68. The lumen 66 travels the length of the trocar sheath 60 from the distal opening 68 to the stop pad 70. Adjacent the stop pad 70 is a handle 64 having an upper knurled portion 72. On the other side of the handle 64 to the stop pad 70 is a cleaning, or access, port 74. The access port 74 provides communication between the exterior of the trocar sheath to the lumen 66. The access port 74 has a Luer fitting 76 covered by a cap 78. When not in use, the cap 78 covers the Luer fitting 76. When removed, the cap 78 exposes the Luer fitting 76; and various lines or other attachments may be made to the Luer fitting thereby providing communication between the exterior of the trocar sheath 60 to its interior lumen 66.

From the proximate portion of the stop pad 70 to the lumen opening 68, the length of the trocar sheath 60 is the same as that of the dilating obturator shaft 42. When fitted within the trocar sheath 60, the dilating tip 44 of the dilating obturator 40 extends out past the opening 68. The beginning 50 of shaft 42 coincides with the opening 68 so that the dilating tip 44 extends fully outward from the lumen 66.

Figure 3A:
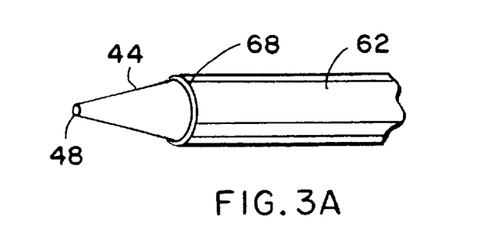
FIGS. 3A and 3B show the tip of the trocar obturator with the stylet tip retracted and exposed, respectively.
Figure 3B:
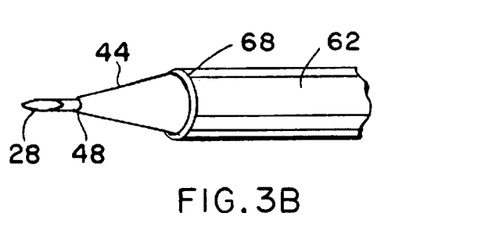

When assembled, FIGS. 3A and 3B show in detail the operating end of the trocar obturator 20.

In FIG. 3A, the cutting tip 28 of the stylet 22 is retracted within the dilating obturator 40 or the dilating tip 44. In FIG. 3B, the cutting tip 28 is exposed out past the aperture 48 of the dilating tip 44.

Figure 4:
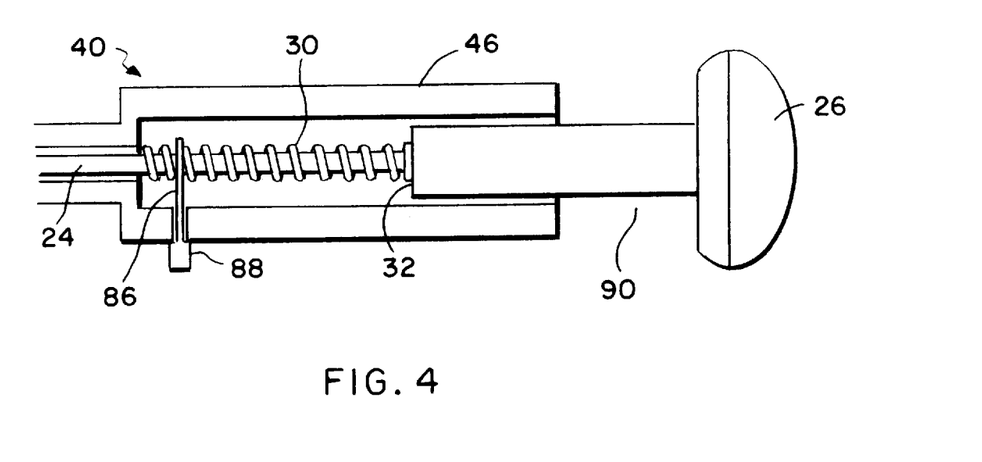
FIG. 4 shows in cross section the stylet handle and spring within the dilating obturator with the spring clip in place about the stylet shaft.
Figure 4A:
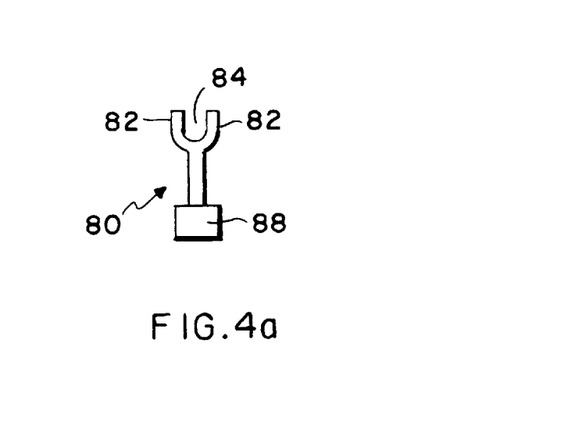
FIG. 4A shows a plan view of the spring clip.

Referring now to FIG. 4, in order to secure the retraction spring 30 with respect to the stop block 46 of the dilating obturator 40, a clip 80 may be inserted through the side of the stop block 46 to surround the stylet shaft 24. Prongs 82 present at the end of the clip 80 define a gap 84 through which the stylet shaft 24 may pass. As the stylet shaft 24 passes through the gap 84, the retraction spring 30 is held relatively in place by the prongs 82 and is thereby coupled to the stop block 46 of the dilating obturator 40. The clip 80 may be disengaged from about the stylet shaft 24 so that the narrow stylet 22 may move freely within or be removed from the dilating obturator 40. Disengagement of the clip 80 also allows initial insertion of the narrow stylet 22 into the dilating obturator 40. The clip 80 passes through an opening 86 in the side of the stop block 46. A small button 88 at the end of the clip 80 serves as a handle and a means by which passage of the clip 80 into the stop block 46 may be obstructed as the size of the button exceeds that of the opening 86.

Between the end of the stop block 46 and the beginning of the handle 26, a gap 90 is present that allows the surgeon's fingers and hand to constructively engage the stylet handle 26. The finger gap 90 allows the surgeon to pull upon the handle 26 and either remove the narrow stylet 22 from the dilating obturator 40 or, if the clip 80 is in place about the stylet shaft 24, stretch the retraction spring 30 so that, upon quick release of the handle 26 by the surgeon, the narrow stylet rapidly snaps back into the dilating obturator to throw forward the cutting tip 28 past the aperture 48 of the dilating tip 44.

Should the surgeon desire a trocar obturator having an initially exposed tip that is retractable, the shaft 24 of the stylet 22 may be lengthened several millimeters. Subsequently, when the stylet 22 slides into the dilating obturator 40, the clip 80 may be engaged to the spring 30 after some compression of spring 30 is achieved. The cutting tip 28 will then be exposed past the dilating tip 44. When pressed (as by obstructive tissue), the stylet 22 will resiliently retract into the dilating obturator 40 as the clip 80 will hold the spring 30, allowing the spring 30 to urge cutting tip 28 forward, yet allowing the stylet 22 to retract. Under such circumstances, the spring 30 is attached to handle 26 and means are provided to block the forward motion of the stylet 22 from travelling too far past the aperture 48. Such means include an obstruction or blocker attached to the stop block 46 preventing the forward travel of handle 26.

Figure 5:
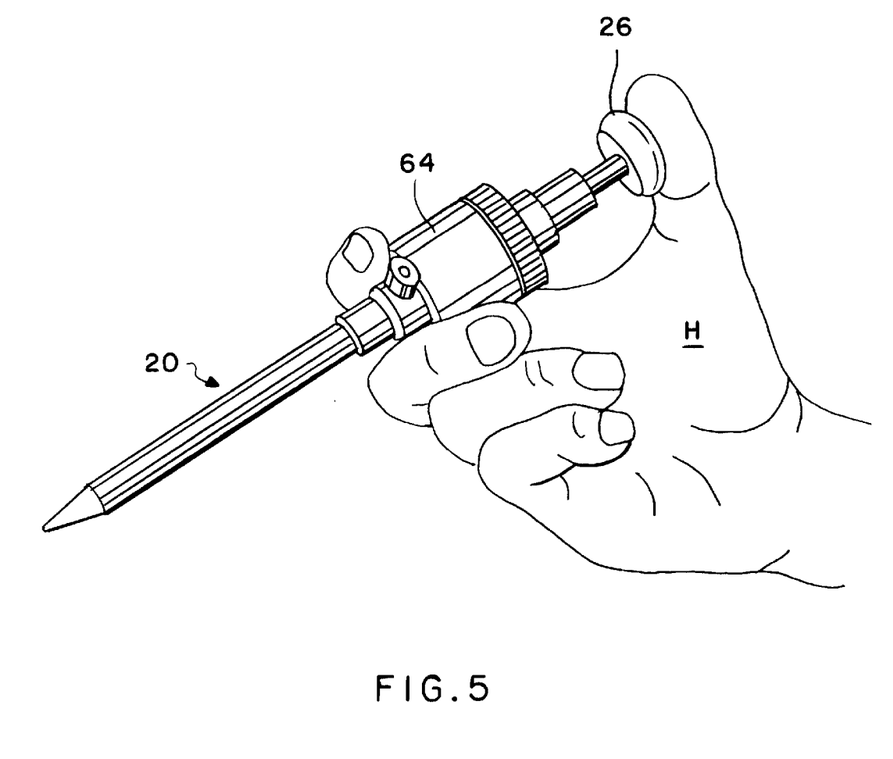
FIG. 5 shows a perspective view of the trocar obturator of the present invention when wielded manually by a surgeon.
Figure 6:
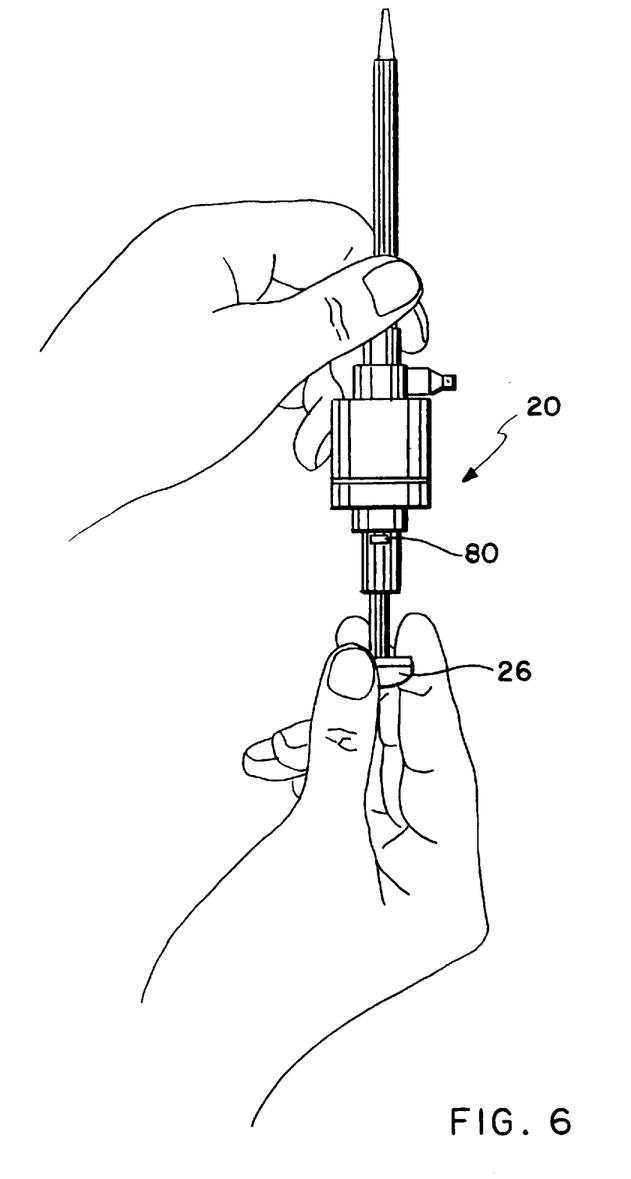
FIG. 6 shows a plan view of a surgeon retracting the stylet.
Figure 7:
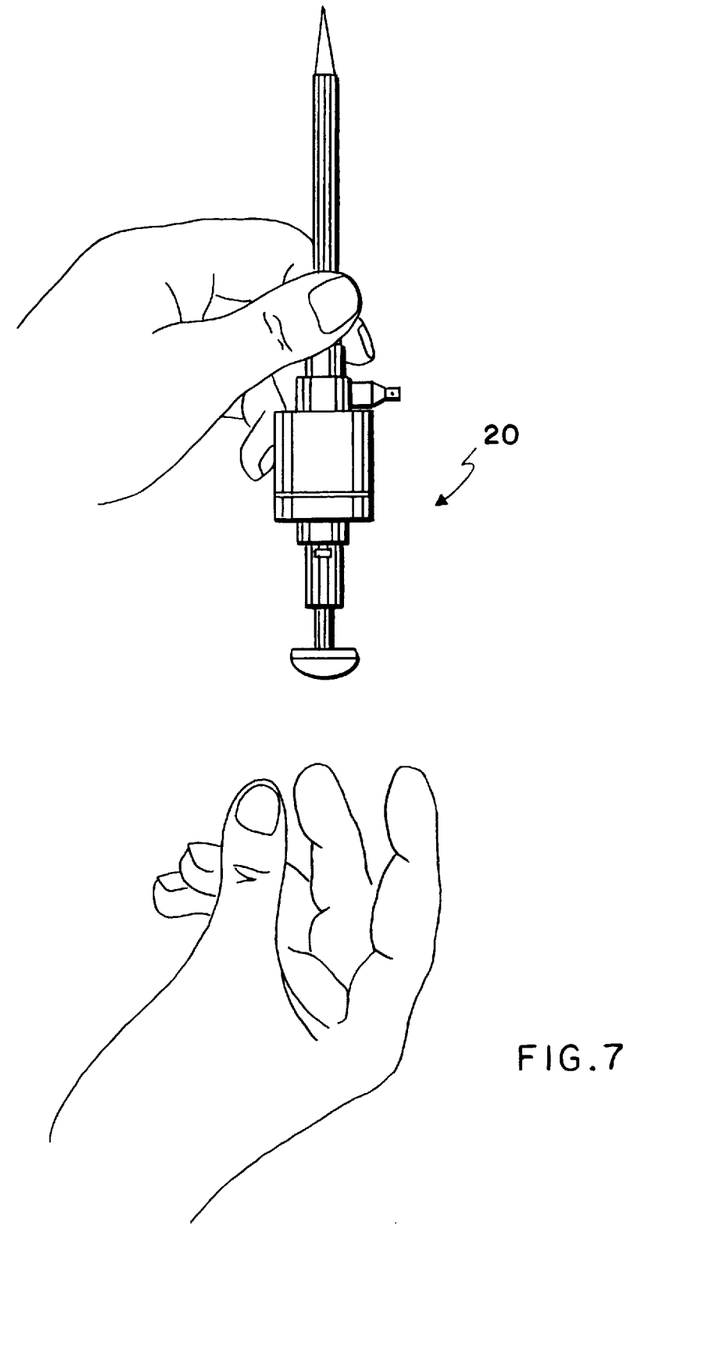
FIG. 7 shows a plan view of the surgeon releasing the stylet handle upon retracting is the stylet so that the cutting tip of the stylet may suddenly and sharply project past the end of the dilating obturator to puncture any obstructive tissue adjacent thereto.

As shown in FIGS. 5, 6, and 7, use of the trocar obturator 20 may be effected by the surgeon using one or both hands.

In FIG. 5, the surgeon may hold the trocar obturator 20 in either hand in order to initially address the exterior of the body cavity to be pierced by the trocar obturator 20. As retraction spring 30 pushes handle 26 out from the dilating obturator 40 while simultaneously retracting the sharp cutting tip 28, the surgeon may grasp the trocar sheath handle 64 while engaging the stylet handle 26 with the thumb. By squeezing together the fingers and thumb, the stylet 22 is forced forward in the dilating obturator 40 so as to expose the cutting tip 28 past the bore aperture 48. This is an initial configuration of the trocar obturator when first used by a surgeon to address the body cavity exterior for subsequent piercing.

The surgeon will then press the sharp operating tip of the trocar obturator 20 against the body cavity. The manual compression of the trocar obturator by the surgeon exposes the cutting tip in a stable configuration. The exposure of the cutting tip is limited by the juncture 32 where the shaft 42 of the dilating obturator prevents further travel of the stylet into the dilating obturator 40 as the shaft 42 engages the handle 26. Other stop means preventing the further travel of the narrow stylet 22 into the dilating obturator 40 may also be achieved and are contemplated in the present invention.

Forward motion into the body cavity by the trocar obturator is achieved by the arm strength of the surgeon and not the hand strength used to squeeze the trocar obturator. Should a sudden slip occur, immediate release of the trocar obturator 20 by the surgeon serves to immediately retract the sharp cutting tip 28 into the dilating obturator 40, preventing any injury to the patient from the cutting tip 28. If during the insertion process the surgeon should encounter obstinate, tough, difficult, or obstructive tissue, instead of using further strength against the tissue by the cutting tip 28, the surgeon may clip the retraction spring into place.

Clipping the retraction spring into place allows the process to occur as shown in FIGS. 6 and 7. Once the clip 80 is set in place, the connection between the retraction spring 30 and the stylet 22 allows displacement of the stylet handle 26 to stretch or compress the retraction spring 30. As shown in FIG. 6, the surgeon may retract the stylet handle 26 away from the stop block 46, thereby stretching the retraction spring 30. The surgeon can determine by sense of touch the response of the retraction spring 30 to the retracting process. Once the surgeon has retracted the stylet handle 26 a sufficient distance, quick release of the stylet handle 26 allows the retraction spring 30 to return to an equilibrium displacement. In doing so, the retraction spring quickly forces, or urges, the narrow stylet 22 into the dilating obturator 40.

The momentum of the narrow stylet 22 and its handle 26 is sufficient to drive the cutting tip 28 forcefully through the bore 52 and past aperture 48 to deliver a short and sharp thrust into the obstructive tissue. As the obstructive tissue will not be able to quickly avoid the high pressure delivered by the cutting tip 28, the obstructive tissue will be either pierced entirely or, at least, cut slightly. If entirely pierced, the obstructive tissue may then be forced aside by the dilating tip 44. If the obstructive tissue is not entirely pierced, the surgeon may press the dilating tip 44 further into the surgical wound and repeat the lancing process until the obstructive tissue is breached and the dilating tip 44 may enter into the body cavity.

Once the puncture wound has been made by the narrow cutting tip 28 of the narrow stylet 22, the narrow stylet 22 may be removed from the trocar obturator 20. This may entail removal of the clip 80 from engagement with the retraction spring 30. Upon removal of the narrow stylet, the narrow stylet 22 may be disposed of; and should a second puncturing procedure be required, an entirely new, fresh, and exceedingly sharp tip may be used to create the second or subsequent puncture into the body cavity.

Once the dilating tip 44 has entered into the body cavity, the surgeon may urge it further into the wound so as to stretch apart the body cavity exterior tissue such as muscles, skin, flesh, and, in the case of the abdominal cavity, the peritoneum. By twisting and pressing the dilating tip 44 into the surgical wound, the trocar obturator will slowly move into the wound and part any cavity exterior tissue until the opening 68 of the trocar sheath 60 passes into the body cavity. The angle at which the dilating tip 44 attacks the surgical wound may be controlled and, preferably, is very gentle in order to provide a smooth transition from the dilating obturator aperture 48 to the trocar sheath's opening 68. Once the opening 68 of the cannula 62 is inserted inside the surgical wound, the dilating obturator 40 may be removed from inside the trocar sheath 60 leaving open the body cavity for laparoscopic or other surgery.

In one embodiment, dilating tip 44 makes an angle of approximately seven degrees (7°) with the shaft 42 and cannula 62. The cutting tip 28 extends past the aperture 48 approximately three tenths of an inch (0.3"). The dilating tip is approximately half an inch (0.5") long. The cannula 62 is approximately three and one-quarter inches (3.25") long and has a diameter of approximately a quarter inch (0.25"). The trocar sheath handle 64 is approximately one and one-half inches (1.5") in length and diameter. The stop pad 70 is approximately one inch (1") in diameter and half an inch (0.5") in length. The stop block 46 is approximately three-quarter inches (0.75") in length. The stylet handle 26 has a radius of approximately half an inch (0.5").

Variation in the dimensions of the present invention are contemplated and include a range of generally from three to thirty degrees (3°–30°) for the dilating tip angle and two to is eight inches (2–8") of length for the cannula 62. Other dimensions may correspondingly vary. The present invention also contemplates use of Verres'-type needle as one alternative embodiment of the narrow stylet 22. When a Verres' needle is used, it should extend onehalf inch (½") or greater beyond the tip 44 of the dilating obturator 40.

Figure 8:
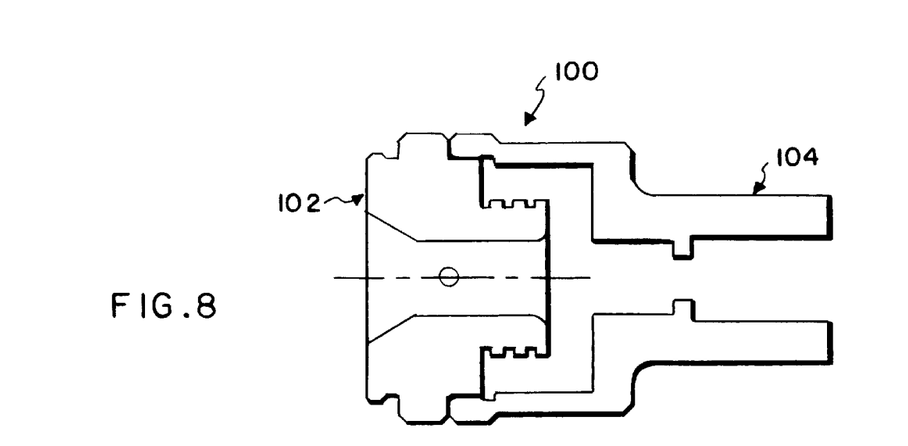
FIG. 8 shows the fitting used to couple the trocar sheath to the dilating obturator so the two do not slip with respect to one another.
Figure 9A:
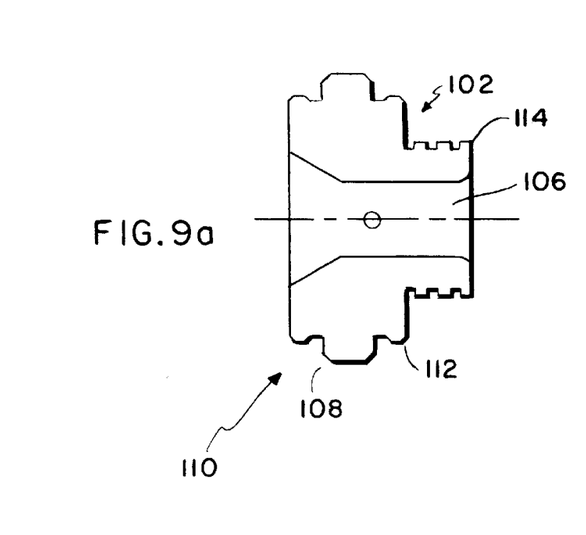
FIGS. 9A and 9B show respectively the cannula cap and the dilating obturator holder shown fitted together in FIG. 8.
Figure 9B:
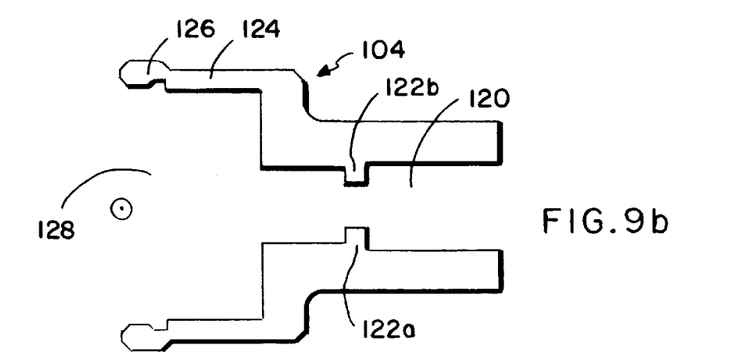

As shown in FIG. 8, the cannula 62 may better engage the dilating obturator 40 by means of a lock fitting 100. As shown in FIGS. 9A–B, the lock fitting has two disconnectable portions: a cannula cap 102 and a holder 104 for the dilating obturator 40.

The cannula cap 102 is generally circular in nature and has a central circular interior channel 106. A flange 108 about one end of the cannula cap 102 has adjacent threads on both sides. One set of threads 110 adjacent the end of the cannula cap 102 serves to allow connection of the cannula 62 to the cannula cap 102. The cannula cap 102 has threads 112 on the side of the flange 108 opposite to the cannula threads 110. The threads 112 serve to allow attachment of the holder 104 to cannula cap 102. A threaded extension 114 extends past the holder threads 112.

Figure 9C:
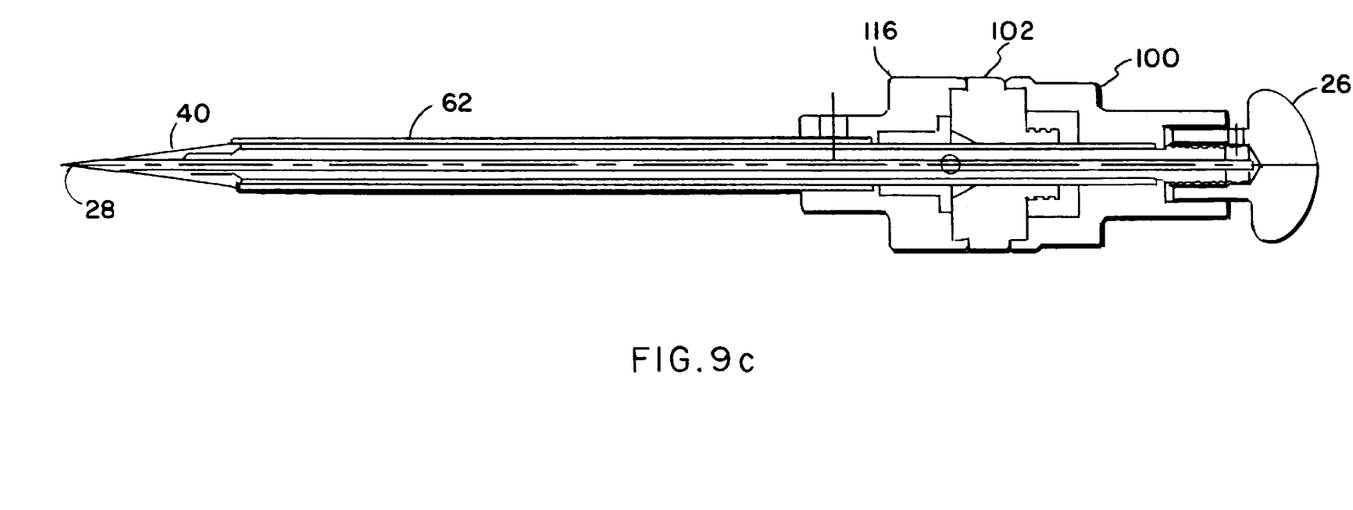
FIG. 9C shows in cross section view a trocar device along the lines of the present invention, showing the cannula cap and dilating obturator holder.

The holder 104 for the dilating obturator 40 is also generally circular in nature and accommodates both the cannula cap 102 and the dilating obturator 40. A central circular interior channel 120 is surrounded by the holder 104. A pair of extensions 122a, b protrude into the central circular channel and serve to engage the dilating obturator 40. An annular extension 124 has a threaded end 126 and circumscribes a void 128 accommodating the threaded extension 114 of the cannula cap 102. The threaded end 126 threadingly engages the holder threads 112 of the cannula cap 102. As shown in FIG. 9C, a cannula fitting 116 completes the set and provides engagement between the cannula 62 and the dilating obturator 40.

Figure 10:
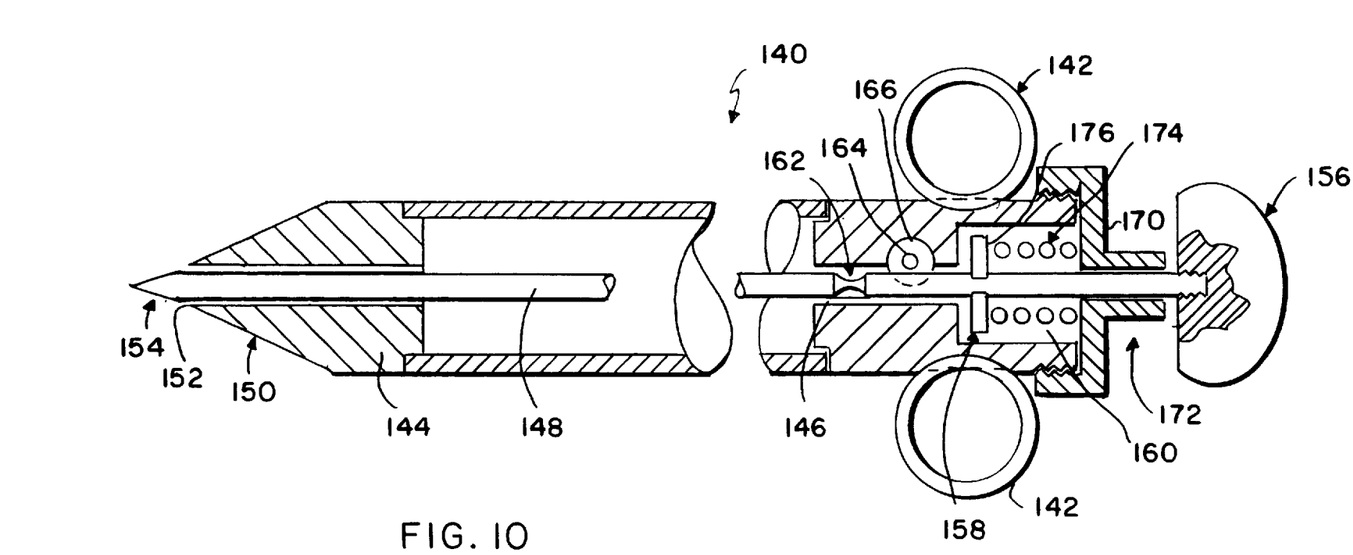
FIG. 10 shows an alternative embodiment of the present invention, using a lock pin to hold in place the retracted stylet.
Figure 12:
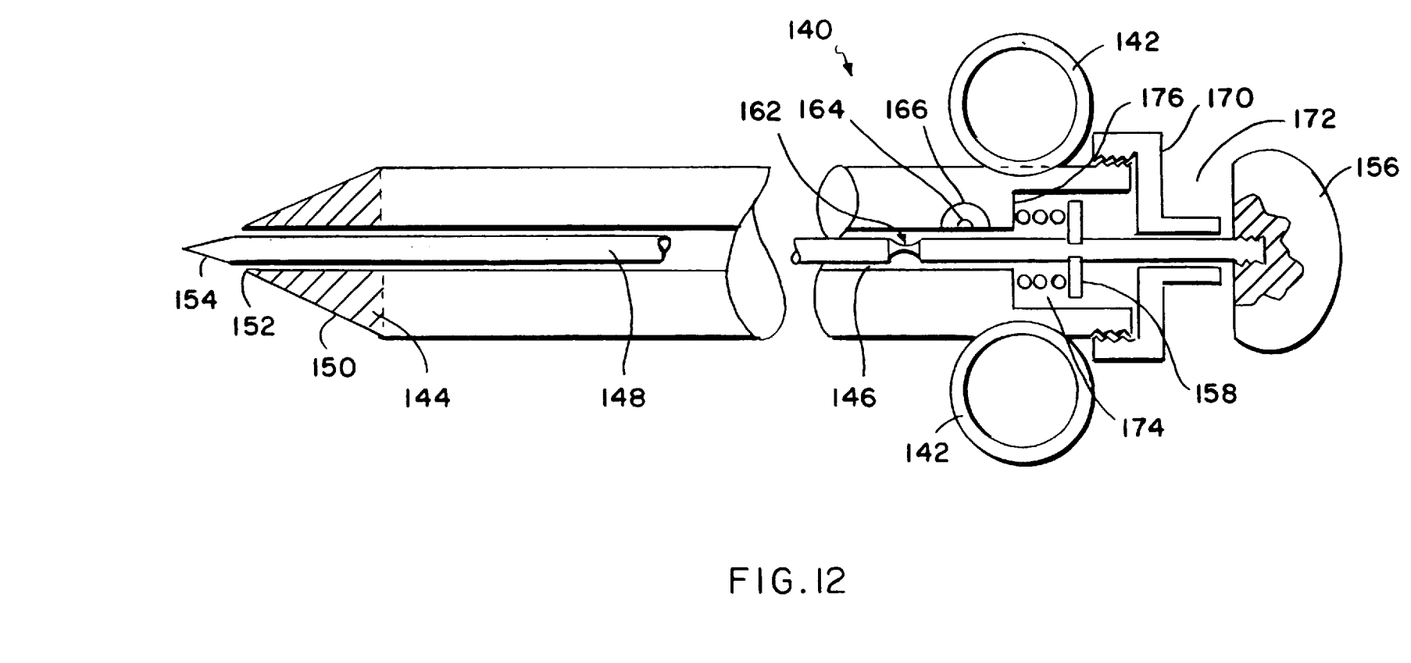
FIG. 12 shows an alternative embodiment of the present invention similar to that shown in FIG. 10, but with the spring pulling the stylet into the dilating obturator.

FIGS. 10 and 12 show an alternative embodiment of the present invention where the stylet shaft can be locked into place upon retraction of the handle. In FIG. 10, the trocar obturator 140 has a diameter of approximately 10 to 15 millimeters and uses finger rings 142 to allow the surgeon to grasp the obturator 140. The body 144 of the obturator 140 is of unitary, or one-piece, construction and has a hollow, central channel 146 through which the stylet 148 may pass through. The dilating tip 150 of the obturator 140 mediates the transition from the aperture 152 of the hollow channel 146 to the full diameter of the trocar obturator 140.

The stylet 148 has an exceedingly sharp cutting tip 154 at the operating end of the trocar obturator 140. Opposite the sharp cutting tip is the handle 156 of the stylet 148. A snap ring 158 is connected about the stylet and moves within a cavity 160 present in the body 144 of the obturator 140. A groove, or notch, 162 is present along the length of the stylet 148 in order to engage a lock pin 164.

The lock pin 164 moves within a bore 166 and the body 144. One end 168 of the lock pin 164 protrudes out the side of the body 144 in order to be engaged by the thumb of the surgeon in order to depress the exposed button 168. Operation of the lock pin 164 is set forth in more detail below.

A cover 170 screws or otherwise attaches to the end of the trocar 140 to enclose the cavity 160. A finger gap 172 is defined between the cover 170 and the handle 156 of the stylet 148. The finger gap allows the surgeon to easily grasp the handle 156 to retract the stylet 148. A spring 174 is held in compression between the snap ring 158 and the cover 170. The spring 174 serves to urge the snap ring 158 away from the cover 170, thereby urging the stylet 148 to extend the cutting tip 154 past the aperture 152.

As shown in FIG. 12, the spring 174 may be attached to the snap ring 158 and the body 144 so that the spring 174 tends to pull the stylet 148 to expose the cutting tip 154 rather than pushing the stylet 148 as is shown in FIG. 10.

As the snap ring 158 is attached to the stylet 148, the force of the spring 174 upon the snap ring 158 serves to urge the stylet tip 154 out past the channel aperture 152. Additionally, the snap ring 158 as well as the handle 156 may serve to limit the extent to which the cutting tip 154 may extend past the aperture 152. When the snap ring 158 comes into contact with the bottom 176 of cavity 160, forward motion of the stylet 148 in the body 144 ceases. Likewise, the same is similarly true when the knob 156 comes into contact with the cover 170.

Figure 11:
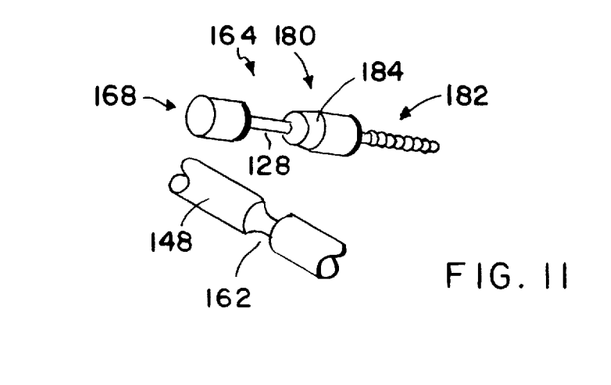
FIG. 11 shows the lock pin and groove structure of the stylet, serving to lock the stylet in place.

FIG. 11 shows in more detail the lock-pin mechanism used in the present invention. As can be seen from FIG. 11, the groove 162 in the stylet 148 may mesh with a similar groove, or notch, 178 present in the lock pin 164. The groove 178 is located between the thumb end of the lock pin 168 and a beveled stop-block portion 180. A lock-pin spring 182 extends past the stop block 180 into the bore 166 to urge the lock pin 164 out and away from the body 144.

In use, the trocar obturator 140 is held by the surgeon and brought to bear against the exterior of the body cavity to be penetrated. Upon contact of the cutting tip 154 with the body cavity exterior, the spring 174 is compressed when obstructive or tough tissue presses against the cutting tip 154. Otherwise, the cutting tip 154 penetrates and pierces adjacent tissue. When an obstruction occurs and cutting ceases, the surgeon may then choose to engage the handle 156 with the palm of the hand, having fingers in the finger rings 142 to keep the cutting tip 154 exposed in order to penetrate the tough, obstructive tissue.

Alternatively, the surgeon may temporarily cease the piercing process and pull the handle 156 back so that the groove 162 is adjacent the lock pin 164. As the spring 174 generally biases the stylet 148 to expose the cutting tip, only upon manual retraction of the stylet by the surgeon would the stylet groove 162 come into alignment with the lock pin 164.

When the groove 162 is adjacent the perpendicular lock pin 164, the stop block 180 is no longer held in place by the wider portions of the stylet 148. The beveled portion 184 can then slip into the groove 162 and is held in place there by the spring 182. The locking of the stylet 148 by the lock pin 164 occurs very quickly and with an audible click and a tactile signal felt throughout the trocar obturator 140. When the stop block 180 fits into the groove 162, release of the handle 156 by the surgeon allows the spring 174 to exert force upon the stop block 180 through the stylet 148. The stop block 180 holds the stylet 148 in a retracted position with stored energy in the spring 174 awaiting to be released.

When the stylet 148 retracts into the body 144 to set the lock pin 164, the tip 154 withdraws from extending past the aperture 152 and, generally, is positioned within the dilating tip 150.

In order to release the stylet 148, the thumb end of the lock pin 168 is depressed by the surgeon's thumb or other finger. Stop block 180 then moves away from the groove 162 until the stop block 180 no longer impedes the stylet. The lock-pin groove 178 is then coincident with the groove 162 with the wider portions of the stylet able to move past the lock-pin groove 178. As the stylet 148 is now allowed to move forward, the energy stored in the spring 174 during the retraction process may now be released; and the cutting tip 154 of the stylet 148 is rapidly thrown forward and past the aperture 152. The forward motion of the stylet 148 is stopped by either the stop ring 158 or the handle 156 when they come into contact with the cavity bottom 176 or the cover 170, respectively. However, as the cutting tip 154 is thrown rapidly forward and into the adjacent tough and obstructive tissue, the force of the rapid release of spring 174 serves to safely cut (to a certain extent) the obstructive tissue. If the tissue is not pierced on the first attempt, the process may be repeated in order to pierce the tissue and to introduce the dilating portion 150.

Once the dilating portion 150 has been introduced into the wound past any obstructive tissue and is in communication with the body cavity, the cover 170 may be detached, as by unscrewing from the unitary body 144, and the stylet 148 removed from the trocar obturator 140. In order to do so, it may be necessary for the surgeon to depress the button 168 to ensure that the lock pin does not engage the stylet 148. The dilation of the wound may then proceed by pressing the blunt dilating portion 150 into the wound.

In an alternative embodiment, the invention shown in FIGS. 11 and 12 may have a second spring that is used to help penetrate tough and obstructive tissues. When the cutting tip 154 is compressed by obstructive tissue to retract the stylet 148, upon the travel of a certain distance by the stylet 148, the second spring can be released manually by the surgeon to transmit its stored energy to the stylet 148.

Note should be taken that the extremely sharp cutting tip of the present invention is never locked in an exposed position. The cutting tip must either be urged forward by the surgeon in order to expose the tip (FIGS. 1–7) or, the cutting tip is resiliently exposed when a stylet 22 of sufficient length is used and retracts under the influence of sufficient obstructing pressure.

While the present invention has been described with regards to particular embodiments, it is recognized that additional variations of the present invention may be devised without departing from the inventive concept.

What is claimed is:

1. A retractable and reusable trocar obturator having a removable tip, comprising:

a trocar sheath having a proximal end and a distal end;
a dilating obturator, said dilating obturator fitting in close relationship within said trocar sheath, said dilating obturator defining a narrow, central, longitudinal bore with proximal and distal apertures, said dilating obturator having a smooth conical tip centered about said distal aperture, said conical tip extending from said distal end of said trocar sheath, said conical tip smoothly mediating a transition between said distal aperture and said distal end of said trocar sheath;
a manually operable narrow stylet, said narrow stylet fitting in close relationship with said dilating obturator, said stylet having an exceedingly sharp, cutting tip; and
biasing means for urging said narrow stylet away from said distal end of said dilating obturator to retract said narrow stylet within said dilating obturator, said biasing means coupled to said narrow stylet; whereby
said narrow stylet fits into said dilating obturator and said dilating obturator fits into said trocar sheath to provide the trocar obturator, said cutting tip of said narrow stylet exposed for puncturing a patient's body cavity when said urging of said biasing means is overcome by manual pressure from a surgeon's hand, said cutting tip then made available for puncturing a body cavity of said patient so that a resulting wound may be dilated by said dilating obturator to ultimately allow said distal end of said trocar sheath to enter said body cavity with minimal patient injury, said cutting tip immediately retracting into said dilating obturator when said manual pressure of said surgeon's hand is removed.

2. The retractable and reusable trocar obturator having a removable tip of claim 1, further comprising:

stop means for blocking further travel of said narrow stylet past said distal aperture of said dilating obturator, said stop means coupled to said narrow stylet; whereby
said cutting tip of said narrow stylet cannot further emerge and travel past said distal aperture despite increased manual pressure delivered by a surgeon's hand upon the trocar obturator or otherwise.

3. The retractable and reusable trocar obturator having a removable tip of claim 2, further comprising:

disengageable coupling means for coupling said biasing means to said dilating obturator, said coupling means disengageably engaging said biasing means and holding an engaged portion of said biasing means stationary with respect to said dilating obturator as said narrow stylet fits within said dilating obturator; whereby
said biasing means urges said narrow stylet to an equilibrium displacement relative to said engaged portion of said biasing means and said narrow stylet is removable from said dilating obturator when said disengageable coupling means disengages said biasing means.

4. The retractable and reusable trocar obturator having a removable tip of claim 2, wherein said biasing means is coupled to said dilating obturator; whereby said narrow stylet may be further retracted into said dilating obturator to displace said biasing means whereupon release of said narrow stylet allows said biasing means to rapidly return to an equilibrium displacement thereby propelling said narrow stylet into said dilating obturator so that said cutting tip may temporarily and forcefully emerge from said distal end of said dilating obturator to puncture any tissue adjacent thereto.

5. The retractable and reusable trocar obturator having a removable tip of claim 4, further comprising:

releasable locking means for releasably locking said narrow stylet in a fixed position upon retraction of said narrow stylet into said dilating obturator; whereby
said releasable locking means may releasably lock said narrow stylet in a position that maintains said biasing means in a displaced condition.

6. The retractable and reusable trocar obturator having a removable tip of claim 5, wherein said selectable locking means further comprises:

said narrow stylet having a narrow neck area defining a groove; and a lock pin, said lock pin adjacent said narrow stylet and biased to engage said groove when said narrow stylet is further retracted into said dilating obturator; whereby upon said engagement of said groove by said lock pin, said narrow stylet is held in a position that displaces said first biasing means and upon disengagement of said lock pin with said groove, said biasing means rapidly returning to an equilibrium displacement, thereby propelling said narrow stylet forcefully towards said distal aperture of said dilating obturator.

7. The retractable and reusable trocar obturator having a removable tip of claim 1, wherein said trocar sheath comprises:

a cannula, said cannula defining a lumen with an aperture to provide said distal end of said trocar sheath;

an access port coupled to said cannula;

a trocar sheath handle, said trocar sheath handle coupled to said cannula proximate said access port; and a stop pad, said stop pad coupled to said cannula proximate said trocar sheath handle;

said lumen passing through said trocar sheath handle and said stop pad.

8. The retractable and reusable trocar obturator having a removable tip of claim 7, wherein said access port comprises a Luer fitting and both said trocar sheath handle and said stop pad are concentric and coaxial with said lumen.

9. The retractable and reusable trocar obturator having a removable tip of claim 1, wherein said smooth conical tip of said dilating obturator is angled in a range from three to thirty degrees (3°–30°).

10. The retractable and reusable trocar obturator having a removable tip of claim 9, wherein said smooth conical tip of said dilating obturator is angled at approximately seven degrees (7°).

11. The retractable and reusable trocar obturator having a removable tip of claim 1, wherein said stylet comprises a Verres'needle.

12. The retractable and reusable trocar obturator having a removable tip of claim 1, wherein said biasing means comprises:

a spring, said spring fixed relative to said stylet and wider than said proximal aperture of said dilating obturator whereby said spring cannot travel into said bore.

13. The retractable and reusable trocar obturator having a removable tip of claim 2, wherein said stop mean for blocking further travel of said narrow stylet comprises:

a stylet handle, said stylet handle at a proximal end of said stylet;

a stop block, said stop block at a proximal end of said dilating obturator; whereby said stop block engages said handle when said narrow stylet slides into said dilating obturator to prevent further travel of said narrow stylet into said dilating obturator.

14. The retractable and reusable trocar obturator having a removable tip of claim 2, wherein said cutting tip of said narrow stylet can only emerge approximately three to four tenths of an inch (0.3–0.4 inch) from said distal aperture.

15. The retractable and reusable trocar obturator having a removable tip of claim 4, wherein said disengageable coupling means comprises a clip, said clip coupled to said dilating obturator and engaging said biasing means.

* * * * *